United States Patent
Woo et al.

(10) Patent No.: US 10,626,427 B2
(45) Date of Patent: Apr. 21, 2020

(54) MUTATED ENZYME OF FLAVIN CONTAINING MONOOXYGENASE WITH INCREASED INDIGO PRODUCTION AND RECOMBINANT MICROORGANISM PRODUCING THE SAME

(71) Applicant: Gyeongbuk Institute for Marine Bioindustry, Uljin-gun (KR)

(72) Inventors: Jung Hee Woo, Uljin-gun (KR); Hae Seon Kim, Uljin-gun (KR); Nyun-Ho Park, Uljin-gun (KR)

(73) Assignee: GYEONGBUK INSTITUTE FOR MARINE BIOINDUSTRY, Uljin-Gun (KR)

( * ) Notice: Subject to any disclaimer, the term of this patent is extended or adjusted under 35 U.S.C. 154(b) by 0 days.

(21) Appl. No.: 16/390,083

(22) Filed: Apr. 22, 2019

(65) Prior Publication Data

US 2019/0323047 A1 Oct. 24, 2019

(30) Foreign Application Priority Data

Apr. 24, 2018 (KR) ........................ 10-2018-0047308

(51) Int. Cl.
| | |
|---|---|
| *C12N 9/04* | (2006.01) |
| *C12P 17/12* | (2006.01) |
| *C12P 17/16* | (2006.01) |
| *C12N 15/52* | (2006.01) |
| *C12N 9/02* | (2006.01) |

(52) U.S. Cl.
CPC .......... *C12P 17/165* (2013.01); *C12N 9/0073* (2013.01); *C12N 15/52* (2013.01); *C12Y 114/13008* (2013.01)

(58) Field of Classification Search
CPC .............................. C12N 9/0006; C12N 15/00
See application file for complete search history.

(56) References Cited

FOREIGN PATENT DOCUMENTS

| KR | 10-1783243 | 9/2017 |
|---|---|---|
| KR | 10-2018-0014637 | 2/2018 |

OTHER PUBLICATIONS

NAD(P)/FAD-dependent oxidoreductase [Celeribacter ethanolicus], NCBI genbank WP_096806729, Oct. 9, 2017.
Hack Sun Choi et al., "A novel flavin-containing monooxygenase from *Methylophaga* sp. strain SK1 and its indigo synthesis in *Escherichia coli*", Biochemical and Biophysical Research Communications, vol. 306, pp. 930-936, 2003.
Choi KY et al., "Molecular cloning and identification of a novel oxygenase gene specifically induced during the growth of *Rhodococcus* sp. strain T104 on limonene.", J Microbiol, vol. 42, No. 2, pp. 160-162, Abstract, 2004.
J.Y. Kim et al., "Multicomponent phenol hydroxylase-catalysed formation of hydroxyindoles and dyestuffs from indole and its derivatives", The Society for Applied Microbiology, Letters in Applied Microbiology, vol. 41, pp. 163-168, 2005.
Kevin E. O'Connor et al., "Indigo Formation by Microorganisms Expressing Styrene Monooxygenase Activity", Applied and Environmental Microbiology, vol. 43, No. 11, pp. 4287-4291, 1997.
Yuanyuan Qu et al., "Influence and optimization of growth substrates on indigo formation by a novel isolate *Acinetobacter* sp. PP-2", Bioresource Technology, vol. 101, pp. 4527-4532, 2010.
Hae-Seon Kim et al., "Complete Genome Sequence of Indigo-Producing Bacterium *Celeribacter* sp. Strain TSPH2", Genome Announc., vol. 5, Issue 45, e01124-17, 2017.
Burt D. Ensley et al., "Expression of Naphthalene Oxidation Genes in *Escherichia coli* Results in the Biosynthesis of Indigo", Science, vol. 222, pp. 167-169, 1983.
N. Doukyu et al., "Isolation of an *Acinetobacter* sp. ST-550 which produces a high level of indigo in a water-organic solvent two-phase system containing high levels of indole", Appl Microbiol Biotechnol, vol. 58, pp. 543-546, 2002.
Juan Pablo Riva Mercadal et al., "Indigo production by *Pseudomonas* sp. J26, a marine naphthalene-degrading strain", Journal of Basic Microbiology, vol. 50, pp. 290-293, 2010.
Hae-Seon Kim et al., "Improved Indigo Productivity of FMO (T424A) Mutated Recombinant *E. coil*", The Posters—The Microbiological Society of Korea, PyeongChang in 2018.
Hae-Seon Kim et al., "Significant Improvement for Indigo from Wild-type Celeribacter to Mutated FMO Recombinant *E. coil*", The Posters—The Microbiological Society of Korea, The Federation of Korean Microbiological Societies, Seoul in 2018.

*Primary Examiner* — Maryam Monshipouri
(74) *Attorney, Agent, or Firm* — Lex IP Meister, PLLC

(57) ABSTRACT

The present invention relates to a mutated protein of FMO derived from *Celeribacter* sp. and a gene encoding the same, a vector comprising the gene, a recombinant cell transformed by the vector, a composition for producing indigo comprising them, and a method for increasing indigo production in the recombinant cell using the transformed recombinant cell.

16 Claims, 9 Drawing Sheets

Specification includes a Sequence Listing.

[FIG. 1]
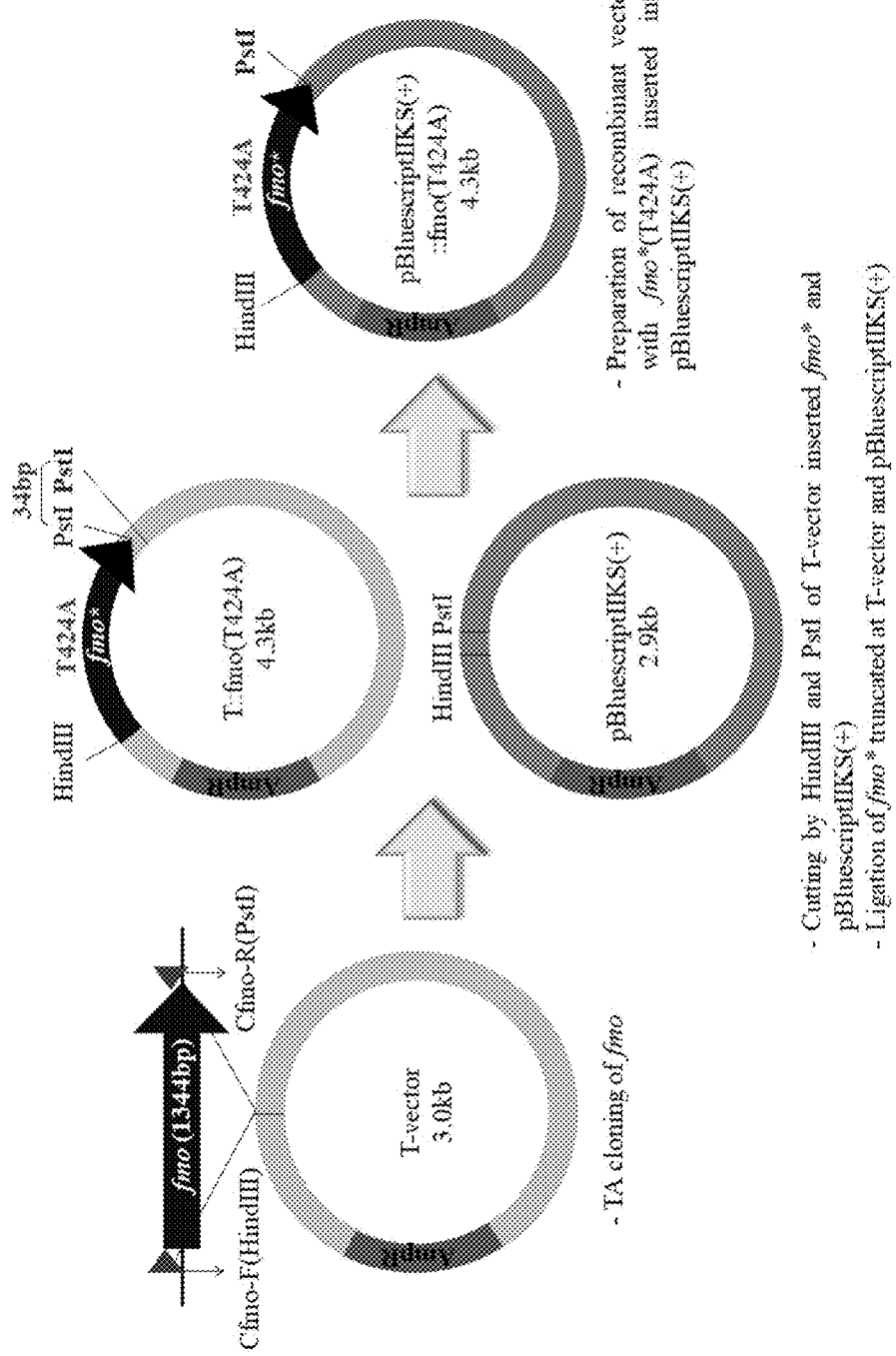

[FIG. 2]

```
FMOori      MTKRVAVIGAGPSGLAQLRAFQSAAQKGAEIPEVVCFEKQSNWGGLWNYTWRTGVDENGE
FMO*T424A   MTKRVAVIGAGPSGLAQLRAFQSAAQKGAEIPEVVCFEKQSNWGGLWNYTWRTGVDENGE
            ************************************************************

FMOori      PVHGSMYRYLWSNGPKEGLEFADYSFEEHFGKQIASYPPRAVLFDYIEGRVIKADVRKWI
FMO*T424A   PVHGSMYRYLWSNGPKEGLEFADYSFEEHFGKQIASYPPRAVLFDYIEGRVIKADVRKWI
            ************************************************************

FMOori      RFSSVIRWVEYDAEKGDFEVTVHDMVEDRVYKERFDNVIIASGHFSSPNVPEYEGFAQFN
FMO*T424A   RFSSVIRWVEYDAEKGDFEVTVHDMVEDRVYKERFDNVIIASGHFSSPNVPEYEGFAQFN
            ************************************************************

FMOori      GRIVHAHDFRDAREFEGKDVLLMGSSYSAEDIGSQCWKYGANSVTTCYRSAPMGFKWPDN
FMO*T424A   GRIVHAHDFRDAREFEGKDVLLMGSSYSAEDIGSQCWKYGANSVTTCYRSAPMGFKWPDN
            ************************************************************

FMOori      WEEKPALQKVEGKIAYFADGSSKDVDAIILCTGYKHYFPFLPDDLRLKTKNRLATADLYK
FMO*T424A   WEEKPALQKVEGKIAYFADGSSKDVDAIILCTGYKHYFPFLPDDLRLKTKNRLATADLYK
            ************************************************************

FMOori      GVVYTHNPKLFYLGMQDQWFTFNMFDAQAWYVRDIILGRIEVPTDKAVLEADVVERVERE
FMO*T424A   GVVYTHNPKLFYLGMQDQWFTFNMFDAQAWYVRDIILGRIEVPTDKAVLEADVVERVERE
            ************************************************************

FMOori      DADDDVKYAIKYQADYVKELVADTDYPSFDIDGACEAFFEWKKHKAKDIMDFRNNSYRSV
FMO*T424A   DADDDVKYAIKYQADYVKELVADTDYPSFDIDGACEAFFEWKKHKAKDIMDFRNNSYRSV
            ************************************************************

FMOori      ITSMAPVHHTPWKDALDDSMEAYLQN
FMO*T424A   ITGMAPVHHTPWKDALDDSMEAYLQN
            ** ***********************
              T424A
```

[FIG. 3]
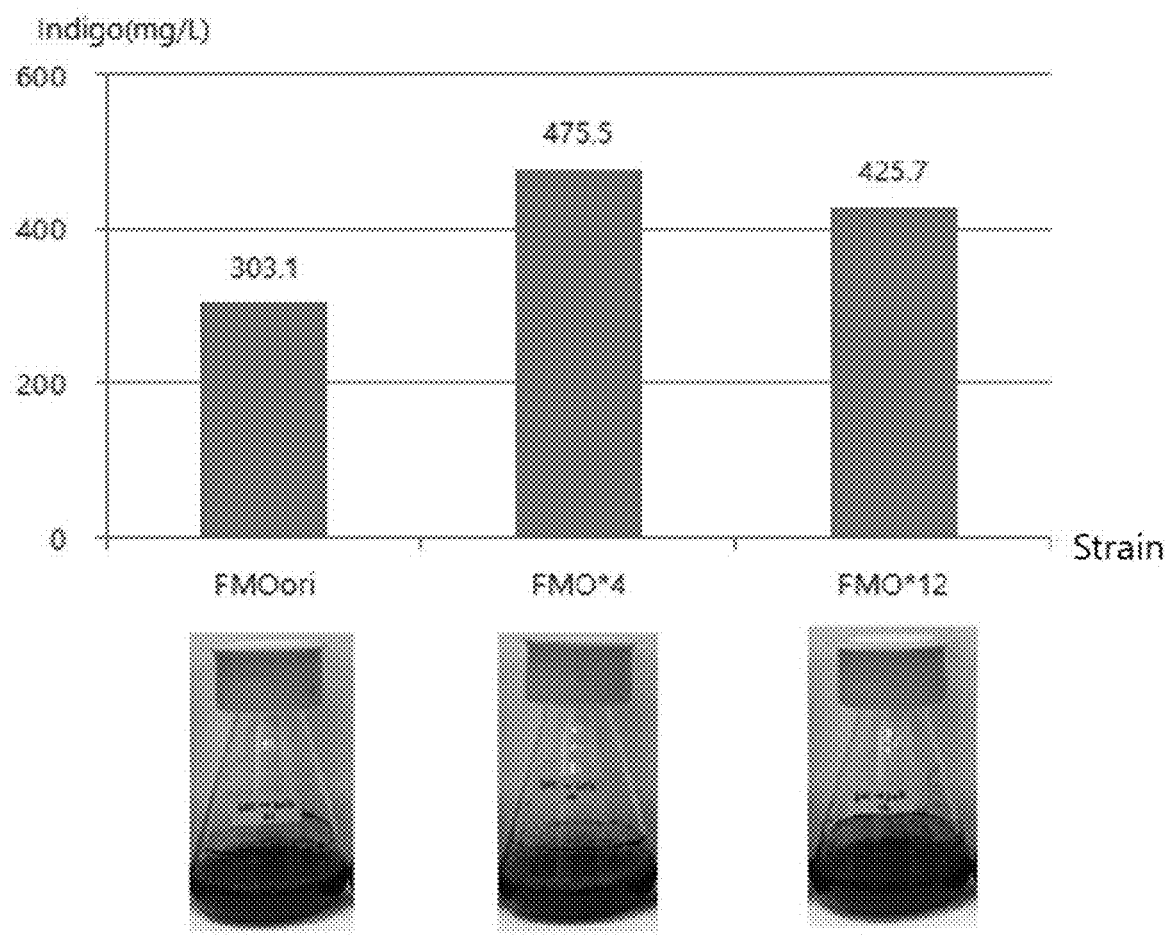

[FIG. 4]
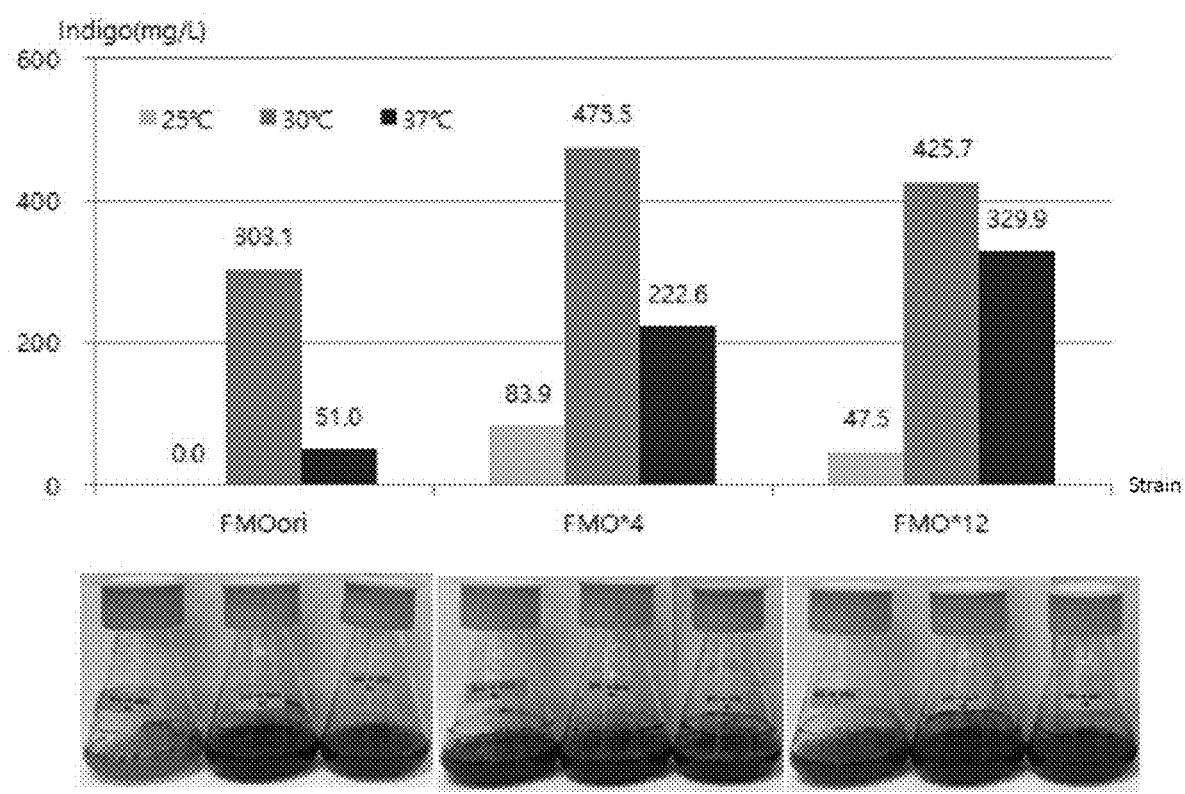
[FIG. 5]
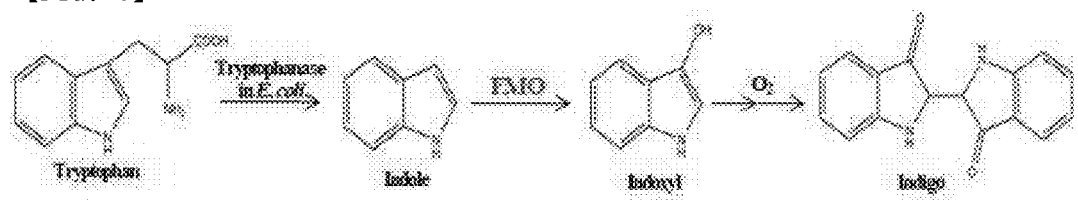

[FIG. 6]
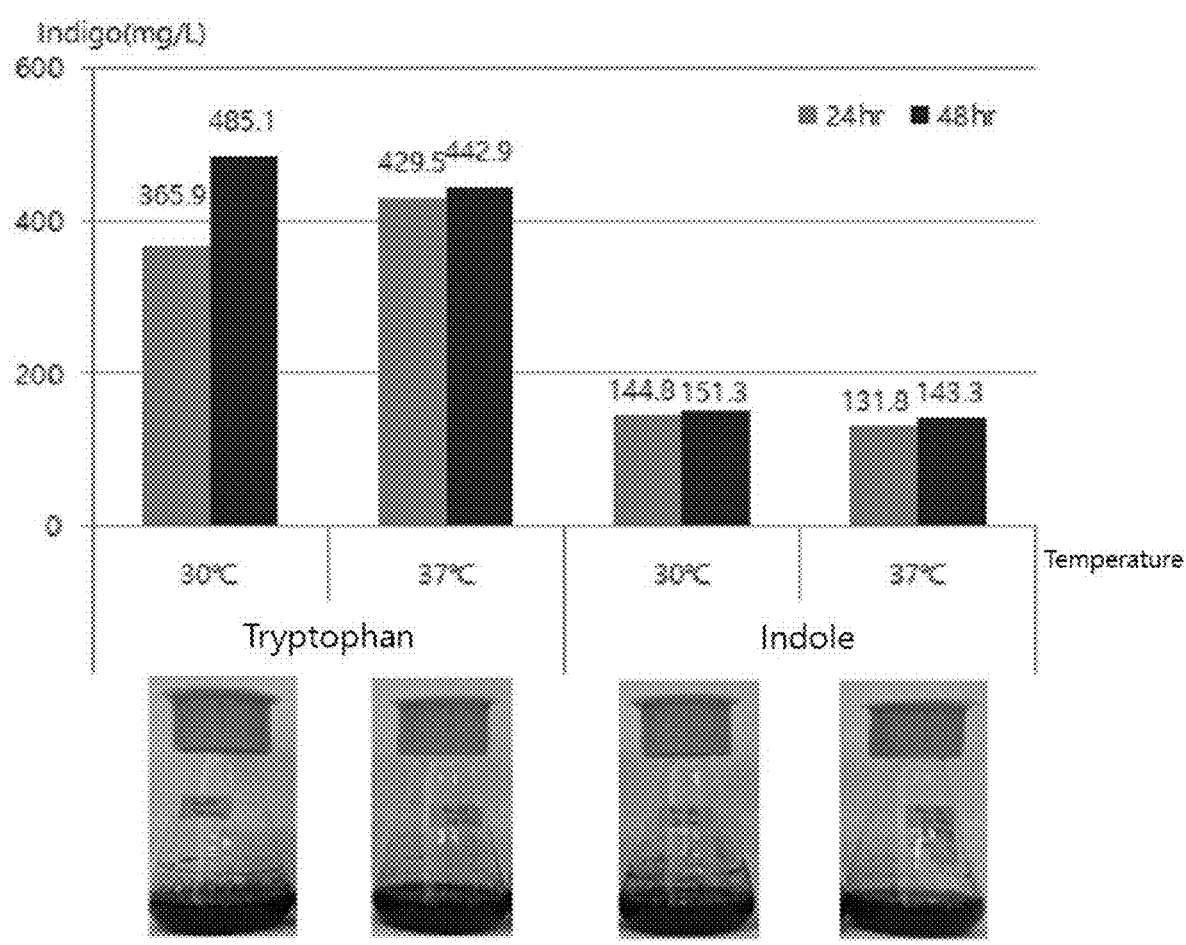

[FIG. 7]
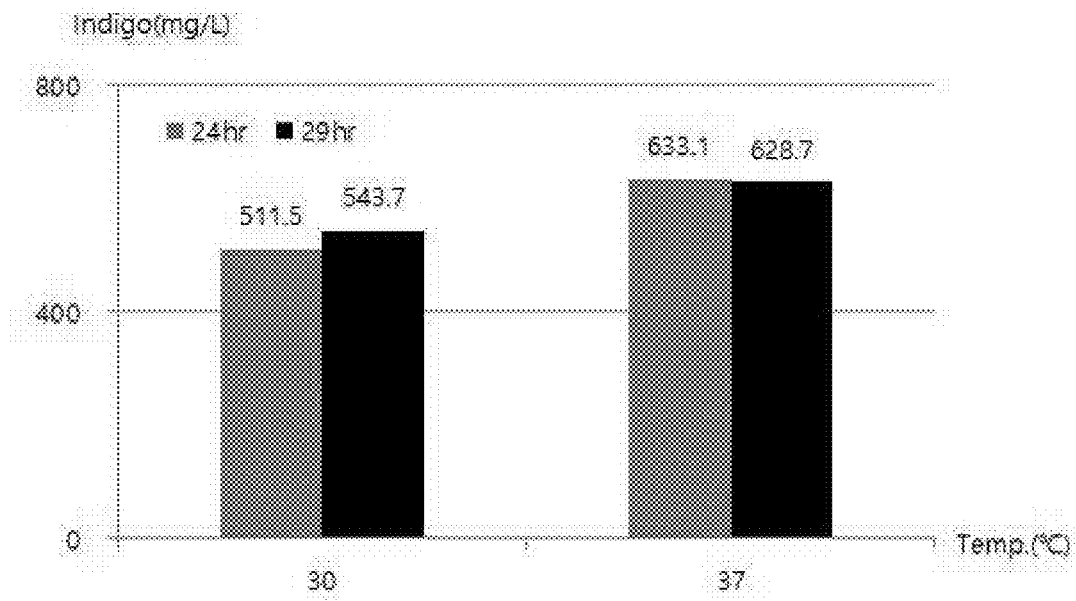
[FIG. 8]
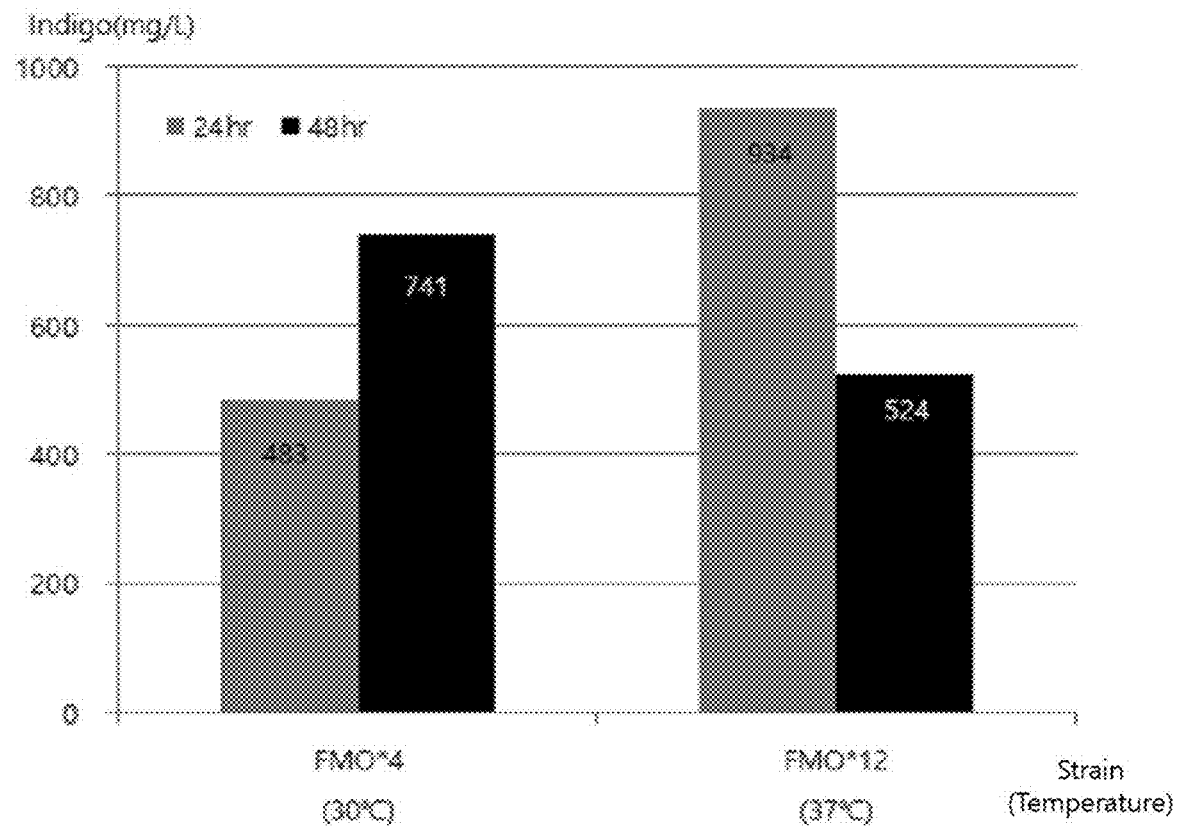

[FIG. 9]

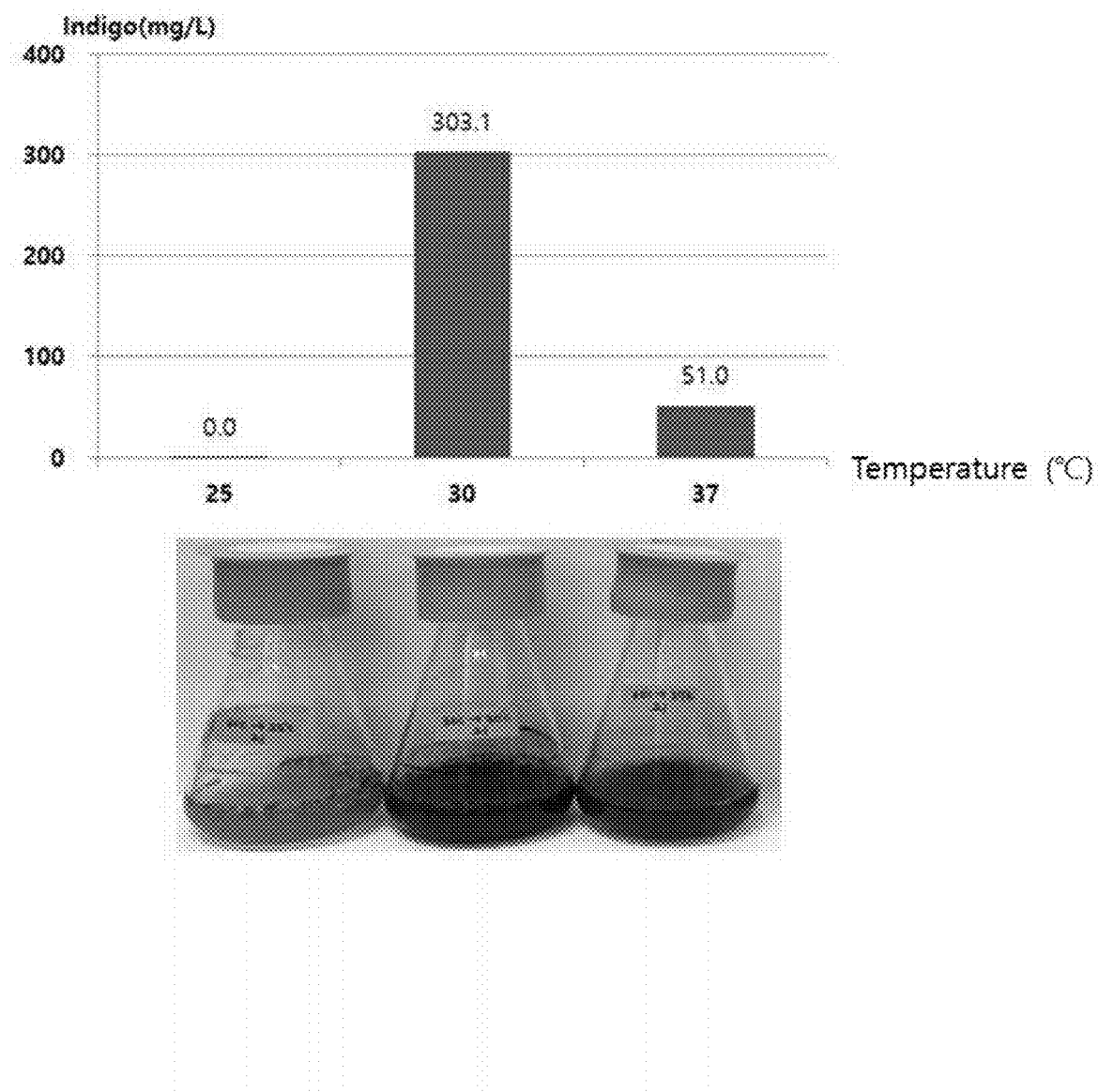
[FIG. 10]

[FIG. 11]
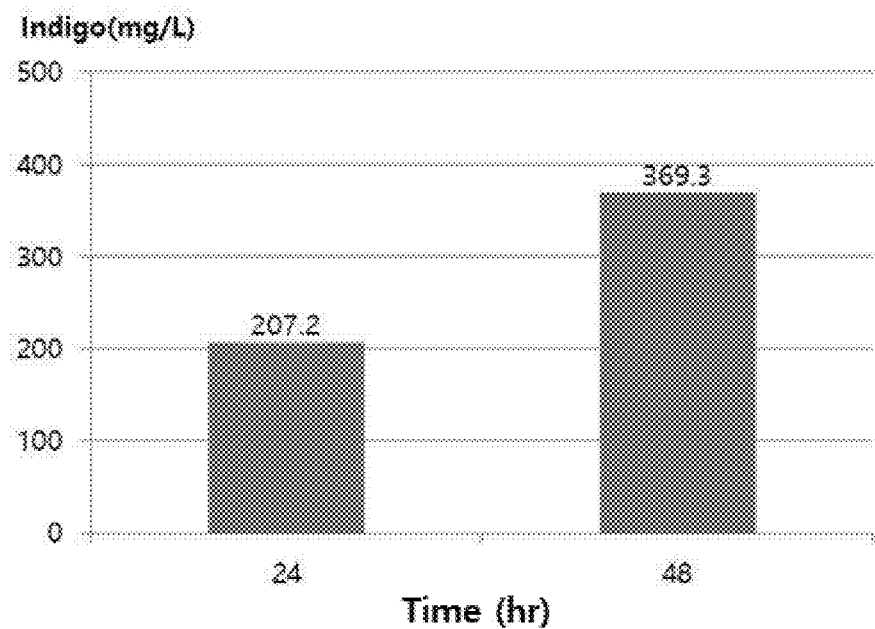
[FIG. 12]
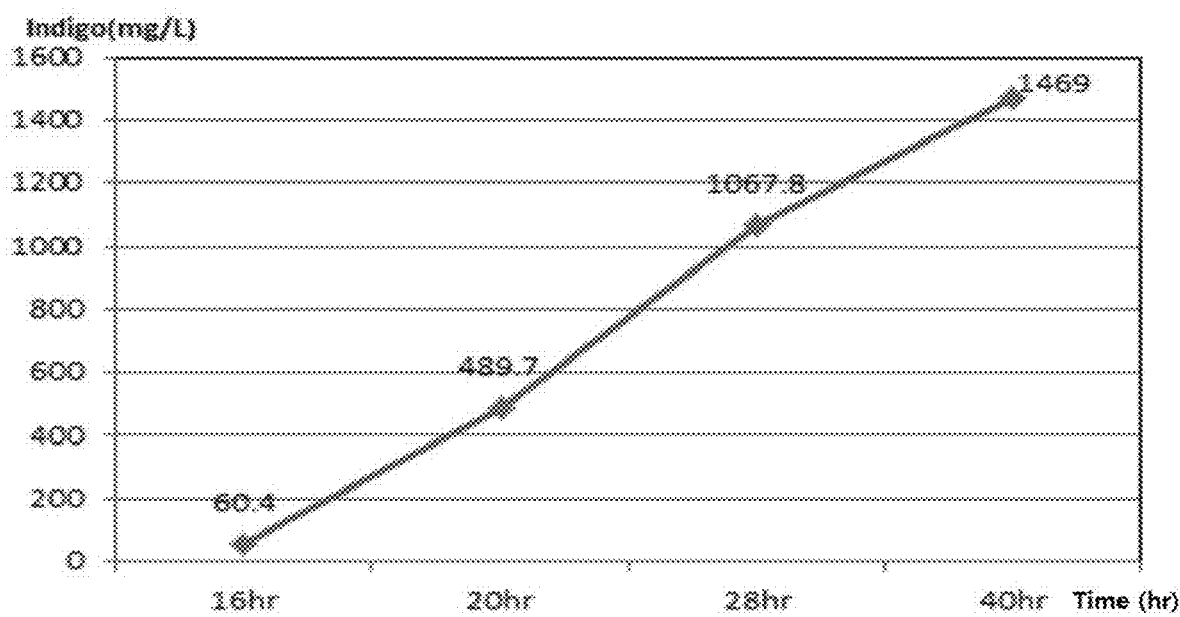

SEQUENCE LISTING

<160> NUMBER OF SEQ ID NOS: 7

<210> SEQ ID NO 1
<211> LENGTH: 447
<212> TYPE: PRT
<213> ORGANISM: Artificial Sequence

```
<220> FEATURE:
<223> OTHER INFORMATION: Amino acid sequence of mutant flavin containing
      monooxygenase(FMO*)

<400> SEQUENCE: 1

Met Thr Lys Arg Val Ala Val Ile Gly Ala Gly Pro Ser Gly Leu Ala
1               5                   10                  15

Gln Leu Arg Ala Phe Gln Ser Ala Ala Gln Lys Gly Ala Glu Ile Pro
            20                  25                  30

Glu Val Val Cys Phe Glu Lys Gln Ser Asn Trp Gly Gly Leu Trp Asn
        35                  40                  45

Tyr Thr Trp Arg Thr Gly Val Asp Glu Asn Gly Glu Pro Val His Gly
    50                  55                  60

Ser Met Tyr Arg Tyr Leu Trp Ser Asn Gly Pro Lys Glu Gly Leu Glu
65                  70                  75                  80

Phe Ala Asp Tyr Ser Phe Glu Glu His Phe Gly Lys Gln Ile Ala Ser
                85                  90                  95

Tyr Pro Pro Arg Ala Val Leu Phe Asp Tyr Ile Glu Gly Arg Val Ile
            100                 105                 110

Lys Ala Asp Val Arg Lys Trp Ile Arg Phe Ser Ser Val Ile Arg Trp
        115                 120                 125

Val Glu Tyr Asp Ala Glu Lys Gly Asp Phe Glu Val Thr Val His Asp
    130                 135                 140

Met Val Glu Asp Arg Val Tyr Lys Glu Arg Phe Asp Asn Val Ile Ile
145                 150                 155                 160

Ala Ser Gly His Phe Ser Ser Pro Asn Val Pro Glu Tyr Glu Gly Phe
                165                 170                 175

Ala Gln Phe Asn Gly Arg Ile Val His Ala His Asp Phe Arg Asp Ala
            180                 185                 190

Arg Glu Phe Glu Gly Lys Asp Val Leu Leu Met Gly Ser Ser Tyr Ser
        195                 200                 205

Ala Glu Asp Ile Gly Ser Gln Cys Trp Lys Tyr Gly Ala Asn Ser Val
    210                 215                 220

Thr Thr Cys Tyr Arg Ser Ala Pro Met Gly Phe Lys Trp Pro Asp Asn
225                 230                 235                 240

Trp Glu Glu Lys Pro Ala Leu Gln Lys Val Glu Gly Lys Thr Ala Tyr
                245                 250                 255

Phe Ala Asp Gly Ser Ser Lys Asp Val Asp Ala Ile Ile Leu Cys Thr
            260                 265                 270

Gly Tyr Lys His Tyr Phe Pro Phe Leu Pro Asp Asp Leu Arg Leu Lys
        275                 280                 285

Thr Lys Asn Arg Leu Ala Thr Ala Asp Leu Tyr Lys Gly Val Val Tyr
    290                 295                 300

Thr His Asn Pro Lys Leu Phe Tyr Leu Gly Met Gln Asp Gln Trp Phe
305                 310                 315                 320

Thr Phe Asn Met Phe Asp Ala Gln Ala Trp Tyr Val Arg Asp Ile Ile
                325                 330                 335

Leu Gly Arg Ile Glu Val Pro Thr Asp Lys Ala Val Leu Glu Ala Asp
            340                 345                 350

Val Val Glu Arg Val Glu Arg Asp Ala Asp Asp Val Lys Tyr
        355                 360                 365        Tyr

Ala Ile Lys Tyr Gln Ala Asp Tyr Val Lys Glu Leu Val Ala Asp Thr
    370                 375                 380

Asp Tyr Pro Ser Phe Asp Ile Asp Gly Ala Cys Glu Ala Phe Phe Glu
```

| | | | | | 385 | | | | | 390 | | | | | 395 | | | | | 400 |
Trp Lys Lys His Lys Ala Lys Asp Ile Met Asp Phe Arg Asn Asn Ser
                    405                 410                 415

Tyr Arg Ser Val Ile Thr Gly Ala Met Ala Pro Val His His Thr Pro
                420                 425                 430

Trp Lys Asp Ala Leu Asp Asp Ser Met Glu Ala Tyr Leu Gln Asn
                435                 440                 445

<210> SEQ ID NO 2
<211> LENGTH: 1402
<212> TYPE: DNA
<213> ORGANISM: Artificial Sequence
<220> FEATURE:
<223> OTHER INFORMATION: Nucleotide sequence encoding mutant flavin
      containing monooxygenase(FMO*4)

<400> SEQUENCE: 2

```
aagcttaaca cacgctcaac caacgggagt tatcaatatg accaaacgag tcgccgtcat    60
cggtgctggc ccctccggcc tcgctcaact gcgtgccttc caatccgccg cccaaaaggg   120
cgccgagatc ccggaagtcg tctgtttcga gaagcaatcg aactggggcg ggctgtggaa   180
ctacacctgg cgcaccggcg tcgatgagaa tggcgaacct gtgcacgggt ctatgtaccg   240
ctacctctgg tccaatggtc cgaaagaggg tctggaattt gccgactatt cctttgagga   300
acatttcggc aagcaaatcg cctcctaccc gccgcgcgcc gtgctgttcg actacatcga   360
aggccgcgtg atcaaagccg acgtccgcaa gtggattcgc ttctcttccg ttatccgctg   420
ggtcgaatat gacgcagaaa aaggcgactt cgaagtcacc gtgcacgaca tggtcgagga   480
ccgcgtctac aaagagcgtt cgacaatgt gatcatcgcc tccggccact tctcctcccc   540
gaacgtgccg gaatacgaag ggttcgccca gttcaacggc cgcatcgtcc acgcccatga   600
tttccgcgac gcccgcgaat cgaaggcaa ggatgtgctt ttgatgggct cgtcctactc   660
cgccgaagac atcggctcgc agtgctggaa atacggcgcg aactcggtga ccacctgcta   720
ccgctccgcg ccgatgggct ttaaatggcc agacaattgg aagaaaaac cggcgctgca   780
aaaggtcgag ggcaagaccg cttatttgc cgatggctcc tcgaaagacg tcgacgcgat   840
catcctgtgc accggctaca acactatt tcccttcctg cccgacgatc tgcgcctcaa   900
gaccaagaac cgtctggcga ccgccgatct ctacaaaggt gtggtctaca cccacaatcc   960
aaagctcttc tacctcggca tgcaggacca gtggttcacc ttcaacatgt cgacgcgca  1020
ggcgtggtat gtgcgggaca tcattcttgg ccgcatcgag gttccgaccg acaaagccgt  1080
tttggaggcc gacgttgtgg aacgtgtgga gcgcgaagac gccgatgacg atgtgaaata  1140
cgcgatcaaa tatcaggccg attacgtcaa ggaactggtg ccgacaccg actaccgtc  1200
cttcgacatc gacggcgcct gcgaggcctt cttcgagtgg aagaaacaca aggcgaaaga  1260
catcatggac ttccgcaaca actcctaccg ttcggtcatc accggcgcca tggcgcctgt  1320
gcaccacacg ccctggaaag acgcgctgga cgacagcatg gaagcctatt tgcagaacta  1380
accgatcttc gcgtccctgc ag                                           1402
```

<210> SEQ ID NO 3
<211> LENGTH: 1436
<212> TYPE: DNA
<213> ORGANISM: Artificial Sequence
<220> FEATURE:
<223> OTHER INFORMATION: Nucleotide sequence encoding mutant flavin
      containing monooxygenase(FMO*12)

<400> SEQUENCE: 3

```
aagcttaaca cacgctcaac caacgggagt tatcaatatg accaaacgag tcgccgtcat      60
cggtgctggc ccctccggcc tcgctcaact gcgtgccttc aatccgccg cccaaaaggg     120
cgccgagatc ccggaagtcg tctgtttcga aagcaatcg aactggggcg ggctgtggaa     180
ctacacctgg cgcaccggcg tcgatgagaa tggcgaacct gtgcacgggt ctatgtaccg     240
ctacctctgg tccaatggtc cgaaagaggg tctggaattt gccgactatt cctttgagga     300
acatttcggc aagcaaatcg cctcctaccc gccgcgcgcc gtgctgttcg actacatcga     360
aggccgcgtg atcaaagccg acgtccgcaa gtggattcgc ttctcttccg ttatccgctg     420
ggtcgaatat gacgcagaaa aaggcgactt cgaagtcacc gtgcacgaca tggtcgagga     480
ccgcgtctac aaagagcgtt tcgacaatgt gatcatcgcc tccggccact tctcctcccc     540
gaacgtgccg aatacgaag ggttcgccca gttcaacggc cgcatcgtcc acgcccatga     600
tttccgcgac gcccgcgaat tcgaaggcaa ggatgtgctt ttgatgggct cgtcctactc     660
cgccgaagac atcggctcgc agtgctggaa atacggcgcg aactcggtga ccacctgcta     720
ccgctccgcg ccgatgggct ttaaatggcc agacaattgg aagaaaaac cggcgctgca     780
aaaggtcgag ggcaagaccg cttattttgc cgatggctcc tcgaaagacg tcgacgcgat     840
catcctgtgc accggctaca acactatttt tcccttcctg cccgacgatc tgcgcctcaa     900
gaccaagaac cgtctggcga ccgccgatct ctacaaaggt gtggtctaca cccacaatcc     960
aaagctcttc tacctcggca tgcaggacca gtggttcacc ttcaacatgt cgacgcgca    1020
ggcgtggtat gtgcgggaca tcattcttgg ccgcatcgag gttccgaccg acaaagccgt    1080
tttggaggcc gacgttgtgg aacgtgtgga gcgcgaagac gccgatgacg atgtgaaata    1140
cgcgatcaaa tatcaggccg attacgtcaa ggaactggtg gccgacaccg actaccgtc    1200
cttcgacatc gacggcgcct gcgaggcctt cttcgagtgg aagaaacaca ggcgaaaga    1260
catcatggac ttccgcaaca actcctaccg ttcggtcatc accggcgcca tggcgcctgt    1320
gcaccacacg ccctggaaag acgcgctgga cgacagcatg gaagcctatt tgcagaacta    1380
accgatcttc gcgtccctgc aggcataatc actagtgaat tcgcggccgc ctgcag       1436
```

<210> SEQ ID NO 4
<211> LENGTH: 447
<212> TYPE: PRT
<213> ORGANISM: Artificial Sequence
<220> FEATURE:
<223> OTHER INFORMATION: Amino acid sequence of wild type flavin
    containing monooxygenase(FMO) from Celeribacter sp. TSPH2

<400> SEQUENCE: 4

```
Met Thr Lys Arg Val Ala Val Ile Gly Ala Gly Pro Ser Gly Leu Ala
1               5                   10                  15

Gln Leu Arg Ala Phe Gln Ser Ala Ala Gln Lys Gly Ala Glu Ile Pro
            20                  25                  30

Glu Val Val Cys Phe Glu Lys Gln Ser Asn Trp Gly Gly Leu Trp Asn
        35                  40                  45

Tyr Thr Trp Arg Thr Gly Val Asp Glu Asn Gly Glu Pro Val His Gly
    50                  55                  60

Ser Met Tyr Arg Tyr Leu Trp Ser Asn Gly Pro Lys Glu Gly Leu Glu
65                  70                  75                  80

Phe Ala Asp Tyr Ser Phe Glu Glu His Phe Gly Lys Gln Ile Ala Ser
                85                  90                  95
```

```
Tyr Pro Pro Arg Ala Val Leu Phe Asp Tyr Ile Glu Gly Arg Val Ile
            100                 105                 110

Lys Ala Asp Val Arg Lys Trp Ile Arg Phe Ser Ser Val Ile Arg Trp
        115                 120                 125

Val Glu Tyr Asp Ala Glu Lys Gly Asp Phe Glu Val Thr Val His Asp
    130                 135                 140

Met Val Glu Asp Arg Val Tyr Lys Glu Arg Phe Asp Asn Val Ile Ile
145                 150                 155                 160

Ala Ser Gly His Phe Ser Ser Pro Asn Val Pro Glu Tyr Glu Gly Phe
                165                 170                 175

Ala Gln Phe Asn Gly Arg Ile Val His Ala His Asp Phe Arg Asp Ala
            180                 185                 190

Arg Glu Phe Glu Gly Lys Asp Val Leu Leu Met Gly Ser Ser Tyr Ser
        195                 200                 205

Ala Glu Asp Ile Gly Ser Gln Cys Trp Lys Tyr Gly Ala Asn Ser Val
    210                 215                 220

Thr Thr Cys Tyr Arg Ser Ala Pro Met Gly Phe Lys Trp Pro Asp Asn
225                 230                 235                 240

Trp Glu Glu Lys Pro Ala Leu Gln Lys Val Glu Gly Lys Thr Ala Tyr
                245                 250                 255

Phe Ala Asp Gly Ser Ser Lys Asp Val Asp Ala Ile Ile Leu Cys Thr
            260                 265                 270

Gly Tyr Lys His Tyr Phe Pro Phe Leu Pro Asp Asp Leu Arg Leu Lys
        275                 280                 285

Thr Lys Asn Arg Leu Ala Thr Ala Asp Leu Tyr Lys Gly Val Val Tyr
    290                 295                 300

Thr His Asn Pro Lys Leu Phe Tyr Leu Gly Met Gln Asp Gln Trp Phe
305                 310                 315                 320

Thr Phe Asn Met Phe Asp Ala Gln Ala Trp Tyr Val Arg Asp Ile Ile
                325                 330                 335

Leu Gly Arg Ile Glu Val Pro Thr Asp Lys Ala Val Leu Glu Ala Asp
            340                 345                 350

Val Val Glu Arg Val Glu Arg Glu Asp Ala Asp Asp Val Lys Tyr
        355                 360                 365

Ala Ile Lys Tyr Gln Ala Asp Tyr Val Lys Glu Leu Val Ala Asp Thr
    370                 375                 380

Asp Tyr Pro Ser Phe Asp Ile Asp Gly Ala Cys Glu Ala Phe Phe Glu
385                 390                 395                 400

Trp Lys Lys His Lys Ala Lys Asp Ile Met Asp Phe Arg Asn Asn Ser
                405                 410                 415

Tyr Arg Ser Val Ile Thr Gly Thr Met Ala Pro Val His His Thr Pro
            420                 425                 430

Trp Lys Asp Ala Leu Asp Asp Ser Met Glu Ala Tyr Leu Gln Asn
        435                 440                 445

<210> SEQ ID NO 5
<211> LENGTH: 1344
<212> TYPE: DNA
<213> ORGANISM: Artificial Sequence
<220> FEATURE:
<223> OTHER INFORMATION: Nucleotide sequence encoding wild type flavin
      containing monooxygenase(FMO) from Celeribacter sp. TSPH2

<400> SEQUENCE: 5
atgaccaaac gagtcgccgt catcggtgct ggcccctccg gcctcgctca actgcgtgcc      60
```

```
ttccaatccg ccgcccaaaa gggcgccgag atcccggaag tcgtctgttt cgagaagcaa      120
tcgaactggg gcgggctgtg gaactacacc tggcgcaccg gcgtcgatga aatggcgaa       180
cctgtgcacg ggtctatgta ccgctacctc tggtccaatg gtccgaaaga gggtctggaa     240
tttgccgact attcctttga ggaacatttc ggcaagcaaa tcgcctccta cccgccgcgc     300
gccgtgctgt tcgactacat cgaaggccgc gtgatcaaag ccgacgtccg caagtggatt     360
cgcttctctt ccgttatccg ctgggtcgaa tatgacgcag aaaaaggcga cttcgaagtc     420
accgtgcacg acatggtcga ggaccgcgtc tacaaagagc gtttcgacaa tgtgatcatc    480
gcctccggcc acttctcctc cccgaacgtg ccggaatacg aagggttcgc ccagttcaac    540
ggccgcatcg tccacgccca tgatttccgc gacgcccgcg aattcgaagg caaggatgtg    600
cttttgatgg gctcgtccta ctccgccgaa gacatcggct cgcagtgctg gaaatacggc    660
gcgaactcgg tgaccacctg ctaccgctcc gcgccgatgg gctttaaatg gccagacaat    720
tgggaagaaa accggcgct gcaaaaggtc gagggcaaga ccgcttatttt tgccgatggc    780
tcctcgaaag acgtcgacgc gatcatcctg tgcaccggct acaaacacta ttttcccttc    840
ctgcccgacg atctgcgcct caagaccaag aaccgtctgg cgaccgccga tctctacaaa    900
ggtgtggtct acacccacaa tccaaagctc ttctacctcg gcatgcagga ccagtggttc    960
accttcaaca tgttcgacgc gcaggcgtgg tatgtgcggg acatcattct tggccgcatc   1020
gaggttccga ccgacaaagc cgttttggag gccgacgttg tggaacgtgt ggagcgcgaa   1080
gacgccgatg acgatgtgaa atacgcgatc aaatatcagg ccgattacgt caaggaactg   1140
gtggccgaca ccgactaccc gtccttcgac atcgacggcg cctgcgaggc cttcttcgag   1200
tggaagaaac acaaggcgaa agacatcatg gacttccgca caactcctat ccgttcggtc   1260
atcaccggca ccatggcgcc tgtgcaccac acgccctgga aagacgcgct ggacgacagc   1320
atggaagcct atttgcagaa ctaa                                            1344

<210> SEQ ID NO 6
<211> LENGTH: 28
<212> TYPE: DNA
<213> ORGANISM: Artificial Sequence
<220> FEATURE:
<223> OTHER INFORMATION: Forward primer Cfmo-F(Hind III)

<400> SEQUENCE: 6
atgcaagctt aacacacgct caaccaac                                         28

<210> SEQ ID NO 7
<211> LENGTH: 28
<212> TYPE: DNA
<213> ORGANISM: Artificial Sequence
<220> FEATURE:
<223> OTHER INFORMATION: Reverse primer Cfmo-R(Pst I)

<400> SEQUENCE: 7
atgcctgcag ggacgcgaag atcggtta                                         28
```

MUTATED ENZYME OF FLAVIN CONTAINING MONOOXYGENASE WITH INCREASED INDIGO PRODUCTION AND RECOMBINANT MICROORGANISM PRODUCING THE SAME

TECHNICAL FIELD

The present invention relates to a mutated enzyme of flavin containing monooxygenase (FMO) with increased indigo production and a recombinant microorganism producing the same, and more specifically, relates to a mutated protein of flavin containing monooxygenase derived from *Celeribacter* sp. TSPH2 and a nucleic acid molecule encoding the same, a vector and a recombinant microorganism comprising the nucleic acid molecule, and a method for production of indigo using the recombinant microorganism.

RELATED ART

Indigo is the most widely used blue dye. Traditionally, it has been used by being extracted from plants such as *Polygonum tinctorium, Indigofera tinctor* and *Isatis indigotica*, etc., but it has been mass-produced mainly by chemical methods, since indigo produced in plants is difficult to mass-produce and has difficulties in extraction. However, in this process, there are problems that it generates non-degradable environmental pollutants and requires high energy for synthesis of indigo.

Therefore, a method for producing indigo using a microorganism harmless to the environment has received attention.

The indigo production by a microorganism was first reported in the recombinant *E. coli* strain expressing naphthalene dioxygenase (Ensly B D et al., 1983, Science, 222(4620):167-9), and in recombinant strains in which the expression of dioxygenase or monooxygenase such as phenol hydroxylase, FMO, indole oxygenase, styrene monooxygenase was induced, the indigo productivity has been known. (O'Connor K E et al., 1997, Appl Environ Microbiol., 63(11):4287-91, Choi K Y et al., 2004, J Microbiol., 42(2)160-2, Choi H S et al., 2003, Biochem Biophys Res Commun. 306(4):930-6). In addition, there is a report that indigo was produced also in wild-type strains, *Pseudomonas* sp. and *Acinetobacter* sp. strains (Doukyu N et al., 2002, Appl Microbiol Biotechnol., 58(4):543-6, Mercadal J P et al., 2010, J Basic Microbiol., 50(3):290-3).

On the other hand, the present inventors have disclosed that *Celeribacter* sp. TSPH2 strain is a novel strain having indigo productivity. *E. coli* transformed by the vector comprising fmo gene derived from *Celeribacter* sp. TSPH2 strain had a problem in that it was inadequate for mass-production and industrialization due to reduced capacity of indigo production at a low temperature or a high temperature, and the maintenance cost of the fermenter was increased.

In addition, in order for indigo production through a microorganism to be mass-produced or industrialized, the indigo productivity should be further enhanced, compared with conventional wild-type strains or wild-type enzymes, and there is a need to be able to produce indigo at high and low temperatures.

DISCLOSURE

Technical Problem

One example of the present invention relates to a mutated enzyme of indigo producing FMO protein derived from *Celeribacter* sp. strain TSPH2 and a gene encoding the same.

Another example of the present invention is to provide a vector comprising the gene and a recombinant cell transformed by the vector.

Other example of the present invention is to provide a method for increasing indigo production in the recombinant cell, comprising a step of culturing the recombinant cell.

Other purpose of the present invention is to provide a composition for producing indigo comprising one or more selected from the group consisting of the FMO mutated protein derived from *Celeribacter* sp. strain TSPH2, a gene encoding the same, a vector comprising the gene and a recombinant cell transformed by the vector.

Technical Solution

Accordingly, the present inventors prepared a mutated enzyme of FMO protein derived from *Celeribacter* sp. strain TSPH2, and produced a recombinant strain producing the mutated enzyme, and in addition, produced a strain with increased productivity which can produce indigo under various temperature conditions and produces a large amount of indigo in a short time, thereby completing the present invention.

Another aspect of the present invention relates to an FMO mutated enzyme derived from *Celeribacter* sp. TSPH2 strain.

Other one aspect of the present invention relates to a nucleic acid molecule encoding the FMO mutated enzyme derived from *Celeribacter* sp. TSPH2 strain.

Other one aspect of the present invention relates to a recombinant vector comprising a nucleic acid molecule encoding the FMO mutated enzyme derived from *Celeribacter* sp. TSPH2 strain.

Other one aspect of the present invention relates to a recombinant microorganism producing indigo which comprises a nucleic acid molecule encoding the FMO mutated enzyme derived from *Celeribacter* sp. TSPH2 strain.

Other one aspect of the present invention relates to a method for producing indigo in the recombinant cell, by culturing a recombinant cell transformed by a vector comprising a gene encoding the FMO mutated enzyme derived from *Celeribacter* sp. TSPH2 strain.

It was confirmed that indigo was produced by 934 mg/L (50 L) at maximum by replacing threonine at the position 424 of the FMO protein with alanine. In particular, at 30° C., while the recombinant strain (FMOori) into which the wild-type FMO was introduced produced 370 mg/L (5 L culture) at maximum at 30° C. within 48 hours, FMO*4 strain produced 741 mg/L (50 L culture) at the same temperature within the same time, and FMO*12 strain produced 934 mg/L (50 L culture) indigo at 37° C. within 24 hours. The fact that 900 mg/L or more of indigo can be produced in a short time suggests that the mass-production and industrialization are possible.

In addition, by developing a strain capable of producing indigo even at a high temperature (37° C.) other than 30° C., it is possible to reduce the operation cost of the fermenter by controlling the temperature according to the seasonal change.

Hereinafter, the present invention will be described in more detail.

One example of the present invention relates to an FMO mutated enzyme derived from *Celeribacter* sp. TSPH2. Specifically, the mutated enzyme comprises the amino acid sequence of SEQ ID NO: 1, and for example, it may be a protein consisting of the amino acid sequence of SEQ ID NO: 1. In the mutated protein having SEQ ID NO: 1 of FMO derived from *Celeribacter* sp. TSPH2 of the present invention, the 424th threonine (T) of FMO derived from *Celeribacter* sp. TSPH2 is replaced with alanine (A) (T424A).

Other one example of the present invention relates to a nucleic acid molecule encoding an FMO mutated enzyme derived from *Celeribacter* sp. TSPH2, and for example, it is a nucleic acid molecule encoding the amino acid sequence of SEQ ID NO: 1, and specifically, the nucleotide sequence designating the 424th amino acid may be GCT, GCC, GCA, or GCG. More specifically, it may be an encoding gene of the FMO mutated enzyme having a nucleotide sequence of SEQ ID NO: 2 or SEQ ID NO: 3. The nucleotide sequence of SEQ ID NO: 3 is a nucleic acid molecule comprising 34 bp that is a part of T-vector after the restriction enzyme recognition site of the restriction enzyme PstI at the 3' end in addition to the encoding gene of a mutated enzyme comprising T424A, for example, the nucleotide sequence of SEQ ID NO: 2.

The wild-type FMO enzyme is isolated from *Celeribacter* sp. TSPH2 (accession number KCCM 1874P) or TSPH6 (accession number KCCM 1875P). The *Celeribacter* sp. strain can produce indigo using indole as a substrate since there is no tryptophanase, but in the strain using the recombinant *E. coli*, since *E. coli* has tryptophanase, tryptophan is degraded to produce indole and the indole is converted into indoxyl by the FMO enzyme, thereby synthesizing indigo.

As other one aspect of the present invention, it relates to a recombinant vector comprising a gene encoding the FMO mutated enzyme derived from *Celeribacter* sp. TSPH2 strain.

The gene to be inserted into the recombinant vector is a nucleic acid molecule encoding the amino acid sequence of SEQ ID NO: 1, and for example, it may be a nucleotide sequence of SEQ ID NO: 2 or SEQ ID NO: 3, but not limited thereto, and it may be a gene encoding the FMO mutated protein derived from *Celeribacter* sp. TSPH2 or a construction in which a part of the sequence of other vector is further inserted at the end of the gene. Said other vector may be T-vector, but not limited thereto.

The mutation of the gene inserted to the recombinant vector may be introduced by various methods known in the art. The recombinant vector may be constructed by various methods known in the art.

The present invention relates to a recombinant cell or a recombinant microorganism in which a nucleic acid molecule encoding an FMO mutated enzyme derived from *Celeribacter* sp. TSPH2 is introduced. Specifically, the FMO mutated enzyme or nucleic acid molecule encoding the same are as described above. The method for preparing the transformed or recombinant microorganism may be constructed by various methods known in the art.

The recombinant cell can be used without limitation as long as it is a transformable cell. Preferably, the recombinant cell may be for example, *E. coli* or yeast, but not limited thereto.

The recombinant cell or recombinant strain according to the present invention expresses the FMO mutated enzyme, and produces indigo using indole or tryptophan as a substrate, and for example, the indigo production obtained by culturing at 30° C. for 24 hours in NY medium in which indole of 2 mM concentration is added is 100 to 200 mg/L, and thus it has a characteristic in that the indigo productivity is increased than the wild-type strain and recombinant strain of wild-type enzyme.

The recombinant cell expressing the mutated enzyme according to the present invention has increased indigo production, as it has the indigo production of 100 to 400%, preferably 150 to 400%, more preferably 200 to 400%, based on 100% of the indigo production (mg/L) of the recombinant cell.

The recombinant cell according to the present invention, compared to the recombinant cell expressing the wild-type FMO enzyme of which indigo production is little under the low temperature condition (e.g. 25° C.), the recombinant cell expressing the mutated FMO enzyme according to the present invention can produce indigo under the low temperature condition. The low temperature condition may be 20° C. to 28° C., preferably 23° C. to 27° C.

The recombinant cell expressing the mutated enzyme according to the present invention has increased indigo production, as it has the indigo production of 100 to 800%, 100 to 750%, 100 to 650%, 200 to 800%, 200 to 750%, or 200 to 650%, based on 100% of the indigo production (mg/L) of the recombinant cell expressing the wild-type enzyme, under the high temperature condition, for example, at 28° C. to 40° C., preferably 29° C. to 38° C., or 30° C. to 37° C., for example, 30° C. or 37° C.

The recombinant cell expressing the mutated enzyme according to the present invention can be cultured for 20 hours to 60 hours, preferably 24 to 48 hours, after inoculation, but not limited thereto. In one example of the present invention, in the recombinant cell without the mutation at 24 hours after inoculation, a more significant increase of indigo production was confirmed (Example 6 and FIG. 8).

The recombinant cell expressing the mutated enzyme according to the present invention can produce indigo by culturing in a medium containing indole or tryptophan, and can prepare indigo by converting tryptophan present in the medium into beneficial indole or indole in the medium into indoxyl. After tryptophan is degraded into indole by tryptophanase of *E. coli* and indole is oxidized into indoxyl by FMO, indigo is produced by a natural oxidation reaction (FIG. 5). The culturing may be conducted in a medium known in the art.

The medium may comprise NaCl 0.5 to 1.5% (w/v) and yeast extract 0.2 to 0.8% (w/v). The concentration of tryptophan comprised in the medium may be 0.1 to 1.0% (w/v), or 0.1 to 0.4% (w/v) based on 100 wt % of the medium composition.

As it is easy to maintain the pH, temperature and concentration of components of a medium constant, in case of mass-culturing a strain, a constant concentration of indigo can be produced when the prepared recombinant strain is mass-cultured.

The recombinant cell can produce indigo even in case of mass-culturing, and in one example of the present invention, 633.1 mg/L of indigo was produced at 37° C. at 24 hours in a 5 L Jar scale, and 543.7 mg/L was produced at 30° C. at 29 hours (FIG. 7), and the indigo productivity was increased in the 50 L fermenter more than that under the optimized condition of the recombinant cell without the mutation. Specifically, in one example of the present invention, as the result of culturing the strain transformed by the FMO mutated gene according to the present invention under the condition of maintaining the 30° C. temperature and pH 7 (FMO*4), and increasing the air supply and RPM with the culture time, it was confirmed that indigo was produced by 1469 mg/L when the culture time was 40 hours and the indigo productivity was significantly increased (FIG. 12).

One example of the present invention relates to a method of production of indigo, comprising a step of culturing a recombinant strain which comprises a nucleic acid molecule encoding the mutated enzyme protein and produces indigo. The content of the recombinant strain is as described above.

The recombinant strain may be cultured in a medium comprising indole or tryptophan, and the composition of the medium is as described above. Specifically, the recombinant strain comprising a gene encoding the FMO mutated enzyme protein provided by the present invention can produce indigo by using the indole or tryptophan as a substrate. The concentration of tryptophan comprised in the medium may be 0.1 to 1.0% (w/v), or 0.1 to 0.4% (w/v), based on 100 wt % of the medium composition.

The step of culturing the recombinant strain may be performed under the temperature condition of 20 to 40° C. The temperature of culturing the strain may be a low temperature condition or high temperature condition, and more specifically, the low temperature condition may be 20° C. to 28° C., preferably 23° C. to 27° C., and the high temperature condition means for example, 28° C. to 40° C., 29° C. to 38° C., 30° C. to 37° C., preferably 30° C. or 37° C.

The culture time of the recombinant strain may be appropriately altered by one skilled in the art according to the technological general knowledge in the art to culture, and for example, culturing may be conducted for example, for 20 to 60 hours, preferably 24 to 48 hours, but not limited thereto.

The method for producing indigo provided by the present invention can control the air supply and stirring speed appropriately during culturing the recombinant strain expressing the FMO mutated enzyme protein, and the air supply and stirring speed may be maintained and/or altered during culturing according to the technological general knowledge in the art.

The air supply may be for example, 0.2 to 1.5 vvm, 0.5 to 1.5 vvm, 0.2 to 1.3 vvm, or 0.5 to 1.3 vvm, but not limited thereto. The air supply may be increased slowly or gradually as the culture time passes. When the air supply is increased gradually, the air supply may be increased by for example, 2 to 5 steps, preferably 3 steps.

The stirring speed may be 250 to 750 rpm, 250 to 650 rpm, 250 to 550 rpm, 300 to 750 rpm, 300 to 650 rpm, 300 to 550 rpm or 350 to 500 rpm, but not limited thereto. The stirring speed may be increased slowly or gradually as the time passes. When the stirring speed is increased gradually, the stirring speed may be increased by for example, 2 to 5 steps, preferably 3 steps, and the step of increasing the stirring speed may be controlled with the air supply and/or independently.

In one example of the present invention, a recombinant strain comprising a gene of the FMO mutated enzyme protein (FMO*4) was cultured in a 50 L fermenter with varying the air supply and stirring speed, while maintaining the temperature and pH constant at 30° C. and pH 7, respectively, in 35 L of the culture solution. Specifically, as the air supply and stirring speed with time, under the condition of filtered air 20 L/min(0.57 vvm) and 350 rpm until 16 hours after the start of the culture, the condition of filtered air 30 L/min(0.86 vvm) and 450 rpm over 16 hours to below 24 hours, and the condition of filtered air 35 L/min(1 vvm) and 500 rpm in 24 hours after the culture, the fermenter culture was performed. As a result, the indigo productivity was shown as 1469 mg/L at 40 hours, and the numerical value is about 1.9 times higher than 741 mg/L of indigo produced at 30° C. for 48 hours under the constant stirring speed and air supply conditions of Example 3-4.

Advantageous Effects

The present invention relates to a mutated gene and protein of FMO derived from *Celeribacter* sp. TSPH2, a vector comprising the gene, a method for increasing indigo production in a recombinant cell in which the vector is transformed, and a recombinant cell with increased indigo production, and the recombinant cell transformed by the method can produce large amounts of indigo in a short time at various temperature conditions than without mutation.

BRIEF DESCRIPTION OF DRAWINGS

FIG. 1 is a diagram of the method of production of the recombinant vector into which the mutated fmo gene having a point mutation with T424A is inserted.

FIG. 2 is one example of the mutated enzyme according to the present invention and shows that the threonine (T) at position 424 in the amino acid sequence of the wild-type enzyme is substituted with alanine (A).

FIG. 3 is a graph showing the indigo production as the result of culturing each strain at 30 t for 24 hours. FMO*4 and FMO*12 strains had 57% and 40% higher productivity, respectively, compared to FMOori strain.

FIG. 4 is a graph showing the indigo production when each strain was cultured at 25° C., 30° C. and 37° C., respectively. FMO*4 strain produced 475.5 mg/L indigo at 30° C., and FMO*12 strain produced 329.9 mg/L indigo at 37° C.

FIG. 5 is a simple mimetic diagram of the process of producing indigo from tryptophan.

FIG. 6 is a graph showing the indigo productivity when tryptophan and indole were supplied to FMO*12 strain as a substrate, respectively. FMO*12 strain could use indole as a substrate, but the productivity was significantly lower than tryptophan.

FIG. 7 is a graph showing the indigo productivity when FMO*12 strain was cultured in 5 L Jar. At 24 hours at 37° C., 633.1 mg/L of indigo was produced, and at 29 hours at 30° C., 543.7 mg/L of indigo was produced.

FIG. 8 is the result of comparing indigo productivities by culturing each strain in a 50 L fermenter. FMO*4 strain produced 741 mg/L indigo at 48 hours and FMO*12 strain produced 934 mg/L indigo at 24 hours.

FIG. 9 is a drawing of confirming the indigo productivity in the strains into which an empty vector and the recombinant vector of flavin containing monooxygenase gene derived from *Celeribacter* sp. were transformed, respectively.

FIG. 10 is a drawing of confirming the degree of indigo productivity depending on the temperature conditions in the strain into which the flavin containing monooxygenase gene derived from *Celeribacter* sp. was transformed.

FIG. 11 is a graph showing the indigo produced at 24 and 48 hours by mass-culturing (% L) the strain (FMOori) into which fmo (flavin containing monooxygenase) gene derived from *Celeribacter* sp. was transformed.

FIG. 12 is a graph of the result of qualifying the indigo production by mass-culturing FMO*4 strain in a 50 L fermenter by the method of Example 6.

MODE FOR INVENTION

Hereinafter, the present invention will be described in more detail by the following reference example and examples. However, these examples are only for illustrating the present invention, and the scope of the present invention is not limited by these examples.

Reference Example 1. Wild-Type Strain Having Wild-Type Enzyme

*Celeribacter* sp. TSPH2 is an isolated bacterium which can decompose phenanthrene that is one of poly aromatic hydrocarbons in mudflat in Taean, and it received the accession number KCCM 11874P by depositing to Korean Culture Center of Microorganisms on Jul. 26, 2016.

After culturing using a baffled flask for smooth aeration supply under the condition of 25° C. and 180 rmp in NY (1% (w/v) NaCl, 0.5% (w/v) Yeast extract) medium in which 2.5 mM concentration of indole was added, a part (0.5~1 ml) of the culture solution was collected and centrifuged, and then the supernatant was removed and an analysis sample in which DMSO indigo was completely dissolved was obtained. As the result of qualifying the indigo production by measuring the OD620 nm value using an ultraviolet ray/visible light spectroscope and obtaining a standard concentration graph with synthesized indigo dissolved in DMSO, the indigo production of 13 mg/L was confirmed (Korean Patent Publication No. 10-2018-0014637).

Example 1. Production of Recombinant Strain Having Wild-Type Enzyme (FMOori)

To express the flavin containing monooxygenase (fmo) gene derived from *Celeribacter* sp. strain in *E. coli* by cloning, the experiment as follows was carried out.

In order to clone the flavin containing monooxygenase (fmo) gene derived from *Celeribacter* sp. strain, the genome DNA of *Celeribacter* sp. TSPH2 strain was extracted using the known phenol/chloroform method, and PCR was performed by using the extracted genome DNA as a template and using the primer and Pfu polymerase (Bioneer) disclosed in the following Table 1. The PCR condition was denaturation 95° C. for 5 min/denaturation 95° C. for 20 seconds, annealing 55 for 30 seconds, elongation 72° C. for 1 minute 30 seconds (30 cycle repeats)/elongation 72° C. for 5 minutes.

TABLE 1

| Name | Sequence | SEQ ID NO |
|---|---|---|
| Cfmo-F (HindIII) | 5' atgcaagcttaaca cacgctcaaccaac 3' | 6 |
| Cfmo-R (Pst I) | 5' atgcctgcagggac gcgaagatcggtta 3' | 7 |

For each of the amplified fmo gene derived from *Celeribacter* sp. strain and pBluescript II KS(+) (Agilent Technologies), HindIII enzyme was reacted at 37° C. for 2~3 hours, and PstI enzyme was reacted at 37° C. for 2~3 hours. After the enzyme reaction, it was mixed so that the molar ratio of vector and insert was 1:3, followed by ligation using T4 ligase (Promega), and it was transformed with *E. coli* DH5α and 40 ul of X-gal (20 mg/ml) was spread in an LB (Luria-Bertani) solid medium comprising 100 ug/ml Ampicillin, and then it was cultured overnight, thereby selecting only the white colony among blue or white colonies.

In order to confirm that the transformed strain selected in Example 1-1 produced indigo, by culturing the colony of the transformed strain selected in Example 1-1 and the colony of the vector-only transformed strain as a substrate in NY medium (0.5% Yeast extract, 1% NaCl) in which 0.2% (w/v) tryptophan was added, it was confirmed that only in the culture solution of flavin containing monooxygenase gene recombinant strain derived from *Celeribacter* sp., blue materials were mass-produced. The experimental result was shown in FIG. 9.

Example 2. Production of Recombinant Strain Having Mutated FMO Enzyme

The method of production of a recombinant vector comprising the FMO mutated enzyme gene is as shown in FIG. 1. The used strain was *E. coli* DH5a, and pBluescript II KS(+) (3.0 kb) vector was used.

PCR (TAKARA, ExTaq) for the insert of 1410 bp comprising the fmo gene derived from *Celeribacter* sp. TSPH2 obtained in Reference example 1 (1344 bp, SEQ ID NO: 5) was conducted by using Taq polymerase. In the PCR amplification method, the same primer pair as Example 1 was used and the PCR condition was also same as Example 1, but the elongation time was 45 seconds. Then, it was subcloned into pGEMTeasy (Promega) vector. The insert was cut by using HindIII and PstI restriction enzymes and pBluescript II KS(+) was cut by using the same restriction enzymes to connect them. By transforming with *E. coli* DH5a, the recombinant vector and recombinant stain comprising FMO mutation (FMO*4, FMO*12) were produced.

As the result of confirming the insert sequence to Genotech, Inc. to confirm the accurate sequence of the clone of which insert size was confirmed, FMO*4 and FMO*12 in which adenine (a) at the 1270th position in fmo gene of 1344 bp of SEQ ID NO: 5 that was the sequence of the gene of the wild-type enzyme was substituted with guanine (g) were confirmed. Through this, as can be seen in FIG. 2, the 434th threonine of the FMO enzyme was replaced with alanine (T424A). In addition, in case of FMO*12, after the stop codon, 34 bp that was a portion of T-vector was inserted. It is presumed that this plays a role of a terminator in expression of fmo, and it is presumed that the mutated FMO enzyme is stably expressed at the temperature of 37° C. to enable indigo production.

FMOori recombinant strain: *E. coli* DH5a/pBluescript II KS(+)::fmo from *Celeribacter* sp. TSPH2 (recombinant *E. coli* strain expressing the wild-type enzyme according to Example 1)

FMO*4 recombinant strain: *E. coli* DH5a/pBluescript II KS(+)::fmo*(T424A) *Celeribacter* sp. TSPH2 (recombinant *E. coli* strain expressing the mutated enzyme according to Example 2)

FMO*12 recombinant strain: *E. coli* DH5a/pBluescript II KS(+)::fmo*(T424A) *Celeribacter* sp. TSPH2 and a portion of T-vector at the 3' end, 34 bp additional insertion (recombinant *E. coli* strain expressing the mutated enzyme according to Example 2)

Example 3: Indigo Production of Recombinant Strain 3-1: Indigo Qualification Method The strain culture solution 0.3 to 1 mL was collected and centrifuged at 13,000 rpm for 5 minutes to obtain blue precipitates, and it was washed by aliquoting sterilized triple distilled water 1 mL, and then it was centrifuged at 13,000 rpm for 5 minutes again. After dissolving blue precipitates in dimethyl sulfoxide (DMSO), insoluble microbial cells-indigo lumps were dissolved by ultrasound wave irradiation. Then, to remove the microbial cells, it was centrifuged at 13,000 rpm at 20° C. for 10 minutes, and then for the supernatant in which only indigo was dissolved purely, the 620 nm value was measured by using a ultraviolet ray/visible light spectrophotometer (V630-Bio UV-Vis Spectrophotometer, JASCO). If necessary, the sample was diluted with DMSO and the 620 nm value was measured, and then the dilution factor was multiplied. Indigo was qualified by using a synthetic indigo dissolved in DMSO (sigma-aldrich, 229296, 95%) as a standard concentration graph.

3-2: Flask Culture of Recombinant Strain

As a seed culture, FMOori strain obtained in Example 1 and FMO*4 and FMO*12 strains of Example 2 were cultured at 37° C. or 30° C. overnight (O/N) by adding 100 u/ml Ampicillin into LB (BD) medium of 10 ml in a 50 ml conical tube and then inoculating a single colony.

As a main culture, 30 ml of medium was aliquoted in a 125 ml Erlenmeyer flask, and 0.3 ml of 1% of the obtained culture solution was inoculated and cultured at 25° C., 30° C. and 37° C., respectively. It was cultured by using a baffled flask for 24 hours for smooth aeration supply under the condition of 30° C. and 180 rpm in NY medium in which tryptophan was added. The medium composition for the main culture comprised yeast extract (ACCUMEDIA) 0.5% (w/v), NaCl (Samchun Chemicals) 1% (w/v) and tryptophan (Daejung Chemicals) 0.2% (w/v).

The indigo production qualified in the culture of the three strains was shown in FIG. 3. FIG. 3 is a graph showing the indigo production obtained as the result of culturing each strain at 30° C. for 24 hours.

As shown in FIG. 3, as the result of measuring the indigo production of the recombinant strains, FMOori strain of Example 1 was 303.1 (mg/L), and FMO*4 recombinant strain of Example 3 was 475.5 mg/L, and FMO*12 recombinant strain of Example 4 was 425.7 mg/L. In other words, when the indigo production (mg/L) of FMOori strain producing the wild-type enzyme was set at 100%, FMO*4 and FMO*12 strains producing the mutated enzyme showed the indigo productivity of 157% and 140%, respectively.

3-3: 5 L Fermenter Culture

FMOori strain obtained in Example 1 and FMO*12 strain of Example 2 were seed cultured with the same medium used in Example 3-2.

The medium was added to 5 L JAR (KoBioTech) so that the volume of the main culture became 3 L and the seed culture solution of 30 ml (1%) was inoculated, and it was cultured under the condition of pH 7, 0.8 vvm aeration amount and 500 rpm, and indigo was qualified.

It was confirmed that 207.2 mg/L of indigo was produced when culturing FMOori recombinant strain for 24 hours, and it was confirmed that 369.3 mg/L of indigo was produced when culturing for 48 hours (FIG. 11).

FMO*12 strain, as shown in FIG. 7, produced 633.1 mg/L of indigo at 37° C. at 24 hours and 543.7 mg/L at 30° C. at 29 hours, as the result of comparing the productivities after culturing for 24 hours and 29 hours at 30° C. and 37° C. in the 5 L Jar (FIG. 7).

3-4: 50 L Fermenter Culture

The productivity was confirmed by culturing FMO*4 strain and FMO*12 strain of Example 2 by using a 50 L fermenter at 30° C. and 37° C., respectively.

Specifically, the O/N primary seed culture was performed by adding 100 ug/ml of Ampicillin to an LB medium by the substantially same method as Example 3-2, and the O/N secondary seed culture was conducted by adding 100 ug/ml of Ampicillin to the LB medium o 300 ml in a 1 L flask. As a main culture, to a 50 L fermenter, 30 L medium (1% (w/v) NaCl, 0.5% (w/v) Yeast extract, 0.2% (w/v) Tryptophan) was prepared and 300 ml of the secondary seed culture solution was inoculated, and it was cultured under the condition of Air 1 vvm, 500 rpm and pH7 for 48 hours.

As shown in FIG. 8, it was confirmed that as the result of culturing FMO*4 strain and FMO*12 strain at 30° C. and 37° C., respectively, FMO*4 strain produced 741 mg/L indigo at 30° C. at 48 hours, and FMO*12 strain produced 934 mg/L at 37° C. at 24 hours. These are 2 times and 2.5 times increased values, respectively, compared to FMOori strain of Example 1 which produced 370 mg/L indigo at 30° C. at 48 hours (FIG. 8).

Example 4: Indigo Production with Culture Temperature

FMOori strain obtained in Example 1 and FMO*4 and FMO*12 strains of Example 2 were cultured by using a baffled flask for 24 hours for smooth aeration supply at 180 rpm under the condition of 25° C., 30° C. and 37° C. temperatures in NY medium in which 0.2% (w/v) concentration of tryptophan was added. The indigo production of the culture was qualified by the same method as Example 3-1, and thereby the indigo production qualified in the cultures of the three strains was shown in FIG. 4 and FIG. 10.

FIG. 4 is a graph showing the indigo production when each strain of three kinds was cultured at 25° C., 30° C. and 37° C., respectively, and FIG. 10 is a graph showing the indigo productivity according to the temperature condition of FMOori. FMO*4 strain produced 475.5 mg/L of indigo at 30° C., and FMO*12 produced 329.9 mg/L of indigo at 37° C. In FMOori strain, the indigo productivity at 25° C. and 37° C. except for the temperature of 30° C. was very poor (FIG. 10).

As the result of confirmation in FMO*4 and FMO*12 strains expressing the FMO mutated enzyme, FMOori strain hardly produced indigo at 25° C., but FMO*4 strain and FMO*12 strain produced 83.9 mg/L and 47.5 mg/L, respectively. In addition, in case of 37° C., the level of 329.9 mg/L was shown in FMO*12 strain, and this is an about 5.5 times increased value, compared to 51.0 mg/L of the indigo production of FMOori strain (FIG. 4, FIG. 10).

Example 5. Indigo Production for Indole Substrate

Tryptophan was used as a substrate for indigo production. Tryptophan is decomposed into indole by tryptophanase, and indole is oxidized to indoxyl by FMO, and then indigo is produced by a natural oxidation reaction (FIG. 5). The indigo productivity of each strain when adding indole reacting with FMO directly as a substrate was confirmed.

FMO*4 and FMO*12 strains obtained in Example 2 were cultured by using a baffled flask for smooth aeration supply under the condition of 30° C. and 37° C. and 180 rpm in NY medium in which 2 mM concentration of indole was added. The medium composition for the main culture was yeast extract (ACCUMEDIA) 0.5% (w/v) and NaCl (Samchun Chemicals) 1% (w/v), and Indole (Sigma) 2 mM was also used as a substrate to replace tryptophan.

As the result of culturing FMO*12 strain of Example 2 under the condition of 30° C. and 37° C. after adding 2 mM indole, indole could be used as a substrate for indigo production, but the indigo productivity was significantly low compared to tryptophan (FIG. 6, Table 2).

TABLE 2

| Culture temperature (° C.) | Culture time (hr) | Indigo production (mg/L) with Tryptophan substrate | Indigo production (mg/L) with Indole substrate |
|---|---|---|---|
| 30 | 24 | 365.9 | 144.8 |
| 30 | 48 | 485.1 | 151.3 |
| 37 | 24 | 429.5 | 131.8 |
| 37 | 48 | 442.9 | 143.3 |

Example 6. Indigo Mass-Production Using Recombinant Strain

The indigo productivity was confirmed by performing mass-culture for indigo production by optimizing the culture condition in 50 L JAR, using FMO*4 strain of Example 2 (DH5a/pBluescript::fmo4 recombinant strain). In Table 3, the culture conditions from the seed culture to the main culture were described.

Specifically, the primary seed culture was performed by inoculating a single colony of FMO*4 strain in a 50 mL tube in which 10 ml of LB medium comprising Ampicillin 100 ug/mL was filled, and culturing under the condition of 30° C. and 180 rpm for about 15 hours overnight. Then, the secondary seed culture was performed under the same temperature and rpm conditions as the primary seed culture for 8 hours by putting 350 mL of LB medium in which Ampicillin 100 ug/mL was added into a IL flask, and inoculating 3.5 mL of the primary seed culture, to use for inoculation of the main culture (Table 3 below).

The main culture was performed by putting a 35 L medium to a 50 L fermenter, and the medium was composed of 1% (w/v) NaCl (Samchun), 0.2% (w/v) tryptophan (CJ) and 0.5% (w/v) yeast extract (Neogen). In the medium, 350 mL of the secondary seed culture was inoculated and the cultured for 40 hours, and it was cultured under varying conditions of air supply and stirring speed (rpm). Specifically, as the air supply and stirring speed with time, under the condition of filtered air 20 L/min (0.57 vvm) and 350 rpm until 16 hours after the start of the culture, the condition of filtered air 30 L/min (0.86 vvm) and 450 rpm over 16 hours below 24 hours, and the condition of filtered air 35 L/min (1 vvm) and 500 rpm in 24 hours after the culture, the fermenter culture was performed. The culture temperature was maintained as 30° C., and the pH was maintained at pH 7 by adding IM phosphoric acid.

TABLE 3

| Classification | Condition | Specific description |
| --- | --- | --- |
| Primary seed culture | Medium | LB medium + Amp100 ug/ml |
| | Culture condition | 30° C., 180 rpm |
| | Inoculation | 10 ml/50 ml tube: single colony inoculation |
| | Culture time | Overnight culture (O/N, 15 hr) |
| Secondary seed culture | Medium | LB medium + Amp100 ug/ml |
| | Culture condition | 30° C., 180 rpm |
| | Inoculation | 350 ml/1 L flask: primary seed culture 3.5 ml inoculation |
| | Culture time | 8.5 hr |
| Main culture | Medium | 1% NaCl (350 g), 0.2% Tryptophan (70 g), 0.5% Yeast extract (175 g) |
| | Culture condition | 30° C., pH7/Air (L/min) 20→30 (16 hr)→ 35 (24 hr) RPM 350→450 (16 hr)→ 500 (24 hr) |
| | Inoculation | 35 L/50 L Fermenter: Secondary seed culture 350 ml (1%) inoculation |
| | Culture time | 40 hr |

After 12 hours from the culture, sampling was performed for about 10 ml into a 15 ml falcon tube once every 4 hours, and the indigo sampled in the culture was qualified by the same method as the indigo qualification method of Example 3-1, and the result was shown in the following Table 4.

In the following Table 4 and FIG. 12, the result of qualifying indigo according to the indigo qualification method from the sampled indigo was shown.

TABLE 4

| | Culture time (hr) | | | |
| --- | --- | --- | --- | --- |
| | 16 | 20 | 28 | 40 |
| OD620 | 1.576 | 0.425 | 0.928 | 1.277 |
| Diluted indigo concentration (ug/ml) | 18.13 | 4.90 | 10.68 | 14.69 |
| Indigo concentration in culture solution (ug/ml) | 18.13 | 48.97 | 106.78 | 146.90 |
| Sampling volume (ml) | 1.00 | 3.00 | 3.00 | 3.00 |
| Final indigo concentration (mg/L) | 60.4 | 489.7 | 1067.8 | 1469.0 |

As shown in the Table 4 and FIG. 12, as the result of mass-culturing FMO*4 strain of Example 2 by varying the air supply and stirring speed (rpm) conditions, the indigo productivity was increased by 1,469 mg/L at 40 hours, and thus about 4 times increased indigo productivity was shown in a shorter time, compared to 370 mg/L of the indigo productivity of FMOori strain of Example 1 when cultured at 30° C. for 48 hours. Thus, it can be seen that the indigo productivity of FMO*4 mutated enzyme protein was significantly increased, compared to the wild-type enzyme protein.

In addition, in Example 3-4 in which the air supply and stirring speed were maintained constant, when culturing FMO*4 strain under the condition of Air 1 vvm and 500 rpm at 30° C. for 48 hours, the indigo productivity of 741 mg/L was shown, but in case of culturing for 40 hours of Example 6 in which the air supply and stirring speed were gradually increased, the indigo productivity was increased by 1469 mg/L, and therefore the indigo productivity was increased about 1.9 times, compared to the case where the stirring speed and air supply were constant. Thus, when culturing the recombinant strain, a higher indigo yield can be obtained by increasing the air supply and stirring speed gradually. The mechanism of this result has not been clear yet, but it is predicted that it is because the stirring speed and air supply are gradually increased to prevent reduction of indigo produced already.

The invention claimed is:

1. A mutated enzyme having flavin containing monooxygenase activity (FMO), comprising the amino acid sequence of SEQ ID NO: 1.

2. A nucleic acid molecule encoding the mutated enzyme having flavin containing monooxygenase activity (FMO) according to claim 1.

3. The nucleic acid molecule of claim 2, wherein the nucleic acid molecule comprises the nucleotide sequence of SEQ ID NO: 2.

4. The nucleic acid molecule of claim 2, wherein the nucleic acid molecule comprises the nucleotide sequence of SEQ ID NO: 3.

5. A recombinant vector comprising a nucleic acid molecule encoding the mutated enzyme having flavin containing monooxygenase activity (FMO) according to claim 1.

6. A recombinant microorganism which comprises a nucleic acid molecule encoding the mutated enzyme having flavin containing monooxygenase activity (FMO) according to claim 1.

7. The recombinant microorganism of claim 6, wherein the recombinant microorganism is *E. coli* or yeast.

8. The recombinant microorganism of claim 6, wherein the nucleic acid molecule comprises the nucleotide sequence of SEQ ID NO: 2 or SEQ ID NO: 3.

9. A method for production of indigo, comprising a step of culturing a recombinant microorganism which comprises a nucleic acid molecule encoding the mutated enzyme having flavin containing monooxygenase activity (FMO) according to claim 1 and produces indigo in the presence of indole or tryptophan.

10. The method for production of indigo of claim 9, wherein the concentration of tryptophan is 0.1 to 0.4% (w/v).

11. The method for production of indigo of claim 9, wherein the recombinant microorganism is cultured at the temperature range of 20 to 40° C.

12. The method for production of indigo of claim 9, wherein the recombinant microorganism is cultured for 20 to 60 hours.

13. The method for production of indigo of claim 9, wherein the culturing is carried out in a medium containing 0.5 to 1.5% (w/v) of NaCl and 0.2 to 0.8% (w/v) of yeast extract.

14. The method for production of indigo of claim 9, wherein the nucleic acid molecule comprises the nucleotide sequence of SEQ ID NO: 2 or SEQ ID NO: 3.

15. The method for production of indigo of claim 9, wherein the step of culturing a recombinant microorganism is performed under the condition in which the air supply is 0.3 to 1.5 vvm and the stirring speed is 300 to 600 rpm.

16. The method for production of indigo of claim 15, wherein the air supply and the stirring speed are increased with the culture time.

\* \* \* \* \*